United States Patent
Aström et al.

(10) Patent No.: US 7,369,889 B2
(45) Date of Patent: May 6, 2008

(54) APPARATUS FOR ANALYZING CARDIAC EVENTS

(75) Inventors: Magnus Aström, Lund (SE); Leif Sörnmo, Lund (SE); Anders Björling, Järfalla (SE)

(73) Assignee: St. Jude Medical AB, Jarfalla (SE)

( * ) Notice: Subject to any disclaimer, the term of this patent is extended or adjusted under 35 U.S.C. 154(b) by 218 days.

(21) Appl. No.: 10/521,080

(22) PCT Filed: Apr. 2, 2004

(86) PCT No.: PCT/SE2004/000529

§ 371 (c)(1),
(2), (4) Date: Jan. 12, 2005

(87) PCT Pub. No.: WO2004/093678

PCT Pub. Date: Nov. 4, 2004

(65) Prior Publication Data

US 2005/0256413 A1    Nov. 17, 2005

(30) Foreign Application Priority Data

Apr. 24, 2003    (SE)    .................................... 0301201

(51) Int. Cl.
*A61N 5/04*    (2006.01)
(52) U.S. Cl. .......................................... 600/509; 607/7
(58) Field of Classification Search ................ 600/509, 600/512
See application file for complete search history.

(56) References Cited

U.S. PATENT DOCUMENTS

| | | | | |
|---|---|---|---|---|
| 5,271,411 | A | * 12/1993 | Ripley et al. | ................ 600/515 |
| 5,439,483 | A | * 8/1995 | Duong-Van | ..................... 607/5 |
| 5,638,823 | A | 6/1997 | Akay et al. | |
| 6,393,316 | B1 | 5/2002 | Gillberg et al. | |

(Continued)

FOREIGN PATENT DOCUMENTS

WO    WO 97/39681    10/1997

(Continued)

OTHER PUBLICATIONS

"Improved Wavelet Packet Compression of Electrocardiogram Data, II: Coating of Compressor Output and QRS Clustering," Bradie, SPIEP Proceedings: Wavelet Applications in Signal and Image Processing IV, Aug. 6-9, 1996, pp. 812-821.

(Continued)

*Primary Examiner*—Carl Layno
*Assistant Examiner*—Brian T Gedeon
(74) *Attorney, Agent, or Firm*—Schiff Hardin LLP

(57) ABSTRACT

An apparatus for detecting cardiac events in electrograms has a feature extraction unit that derives features of the cardiac events for discriminating among different types of cardiac events. A clustering unit groups cardiac events with similar features into respective clusters defined by predetermined cluster features. The feature extraction unit determines a feature vector describing waveform characteristics of cardiac events in the electrogram by a wavelet transform. The clustering unit determines the distance between the feature vector and corresponding cluster feature vectors in order to assign the cardiac event in question to that cluster which results in a minimum distance, providing that the minimum distance is less than a predetermined threshold value. A heart stimulator provided with such a cardiac event detecting apparatus detects the occurrence of an arrhythmia and appropriately controls a pulse stimulator to treat the arrhythmia.

13 Claims, 8 Drawing Sheets

U.S. PATENT DOCUMENTS

2004/0096100 A1* 5/2004 Ii et al. .................... 382/159

OTHER PUBLICATIONS

"Wavelet Transform Based Algorithms for EGM Morphology Discrimination For Implantable ICDs," Koyrakh et al, Computers In Cardiology, vol. 26 (1999) pp. 343-346.

"Clustering ECG Complexes Using Hermite Functions and Self-Organizing Maps," Lagerholm et al, IEEE Trans. On Biomedical Engineering, vol. 47, No. 12 (Jul. 2000) pp. 838-848.

"ECG Beat Recognition Using Fuzzy Hybrid Neural Network," Osowski et al, IEEE Trans. On Biomedical Engineering, vol. 48, No. 11 (Nov. 2001) pp. 1265-1271.

"Discrimination of Atrial Fibrillation From Regular Atrial Rhythm by Spatial Precision of Local Activation Direction," Schoenwald et al, IEEE Trans. On Biomedical Engineering, vol. 44, No. 10 (Oct. 1997) pp. 958-963.

"Morphology Discrimination: A Beat-to-Beat Algorithm for the Discrimination of Ventricular from Supraventricular Tachycardia by Implantable Cardioverter Defibrillators," Grönefeld et al, J. Pacing Clin. Eectrophysiol., vol. 24 (Oct. 2001) pp. 1519-1524.

"New Bayesian Discriminator for Dettection of Atrial Tachyarrthyhmias," Xu et al, Circulation, vol. 105 (2002) pp. 1472-1479.

* cited by examiner

APPARATUS FOR ANALYZING CARDIAC EVENTS

BACKGROUND OF THE INVENTION

1. Field of the Invention

The present invention relates to an apparatus for cardiac events detected in electrograms, EGMs, and to a heart stimulator provided with such an apparatus.

In the following the expression "cardiac event" denotes the depolarization phase in the cardiac cycle, which for atrial signals is commonly known as P wave and for ventricular signals as R wave or QRS complex.

2. Description of the Prior Art

In the field of devices for cardiac rhythm management (CRM), accurate rhythm classification is an increasingly important aspect. Pacemakers are primarily used to assist in bradycardia or when the electrical propagation path is blocked, whereas the primary use of implantable cardioverter defibrillators (ICD) is to terminate ventricular arrhythmia, a life-threatening condition if not immediately treated. In both types of devices, accurate event classification of the electrogram signal is needed for identifying, e.g., atrial and ventricular fibrillation in order to give appropriate therapy for the detected arrhythmia. For pacemakers, this may necessitate changing the pacing mode in order to stabilize the ventricular rhythm during an episode of atrial fibrillation. An ICD responds to ventricular fibrillation by giving a defibrillating shock intended to terminate the fibrillation.

Ever increasing demands are put on both kinds of devices to better handle their primary task as well as to manage other tasks than those originally intended for. One such task may be, for an implantable medical device, to identify atrial flutter in order to terminate it by atrial pacing or to defibrillate atrial fibrillation. Although it is not a life-threatening arrhythmia, atrial fibrillation is an inconvenience to the patient and increases the risk for other diseases such as stroke. Atrial pacing may also be one way of terminating supraventricular tachycardias. An ICD specific task is to identify atrial fibrillation in order to not mistake it for ventricular fibrillation and the risk of giving an unnecessary, and possibly harmful, defibrillation shock. Another, more general, utilization is to efficiently store rhythm data for later analysis and evaluation, already done in modern ICD's. By collecting data, better knowledge of the evolution of cardiac diseases and the functionality of the device can be obtained.

Clustering represents an important task within the classification problem where each individual event is assigned to a cluster of events with similar features. Labelling of the clusters, i.e., associating the cluster with a specific cardiac rhythm, completes the classification such that the device can provide proper therapy when needed. However, certain constraints distinguish clustering in CRM devices from clustering in general. In order to give immediate therapy, it requires clustering to be done in real-time, thus excluding many iterative clustering algorithms such as k-means clustering and competitive learning. Various methods have recently been presented concerning clustering of signals from the surface electrocardiogram (ECG), based on, e.g., self-organizing maps or fuzzy hybrid neural networks, see M. Lagerholm, C. Peterson, G. Braccini, L. Edenbrabdt, and L. Sörnmo, Clustering ECG complexes using Hermite functions and self-organizing maps", IEEE Trans. Biomed. Eng., vol. 47, pp. 838-848, July 2000, and S. Osowski and T. Linh, "ECG beat recognition using fuzzy hybrid neural network", IEEE Trans. Biomed. Eng., vol. 48, pp. 1265-1271, November 2001. However, most clustering algorithms used for ECG analysis are computationally rather complex and therefore unsuitable for implantable CRM devices. Furthermore, not much a priori morphologic information is associated with the various rhythms in the electrogram (EGM); this is in contrast to the more well-defined ECG.

Previous work in the area of intracardiac event classification mainly focused on discrimination of a specific condition in order to discern, e.g., atrial fibrillation from other atrial tachyarrythmias, see A. Schoenwald, A. Sahakian, and S. Swiryn, "Discrimination of atrial fibrillation from regular atrial rhythms by spatial precision of local activation direction", IEEE Trans. Biomed. Eng., vol. 44, pp. 958-963, October 1997. Other applications involve discrimination of ventricular from supraventricular tachycardia, see L. Koyrakh, J. Gillberg, and N. Wood, "Wavelet based algorithms for EGM morphology discrimination for implantable ICDs", in Proc. Of Comp. In Card. (Piscataway, N.J., USA), pp. 343-346, IEEE, IEEE Press, 1999, and G. Grönefeld, B. Schulte, S. Hohnloser, H.-J. Trappe, T. Korte, C. Stellbrink, W. Jung, M. Meesmann, D. Böcker, D. Grosse—Meininghaus, J. Vogt, and J. Neuzner, "Morphology discrimination: A beat-to-beat algorithm for the discrimination of ventricular from supraventricular tachycardia by implantable cardioverter defibrillators", J. Pacing Clin. Electrophysiol., vol. 24, pp. 1519-1524, October 2001. More general classification algorithms, which in turn involve training on individual patients, have been based on analog neural networks or wavelet analysis for morphologic discrimination of arrhythmias.

PCT Application WO 97 39 681 describes a defibrillator control system comprising a pattern recognition system. The intracardiac electrogram signal is digitised and delivered for feature selection into a selector. The feature selector outputs selected features to a trained classifier to provide information as to what group the produced signal should be clustered, e.g. ventricular tachycardia. The classifier outputs the classified information for use for a therapeutic decision.

U.S. Pat. No. 5,271,411 discloses an ECG signal analysis and cardiac arrhythmia detection by extraction of features from a scalar signal. A QRS pattern vector is then transformed into features describing the QRS morphology, viz. a QRS feature vector. A normal QRS complex is identified based on the population of QRS complexes located within clusters of QRS features within a feature space having a number of dimensions equal to the number of extracted features. The extracted morphology information is then used for judging whether a heartbeat is normal or abnormal.

U.S. Pat. No. 5,638,823 describes non-invasively detecting of coronary artery diseases. A wavelet transform is performed on an acoustic signal representing one or more sound event caused by turbulence of blood flowing in an artery to provide parameters for a feature vector. This feature vector is used as one input to neural networks, the outputs of which represent a diagnosis of coronary stenosis in a patient.

In Michael A. Unser et al, "Wavelet Applications in Signal and Image Processing IV", Proceedings SPIE—The International Society for Optical Engineering, 6-9 Aug. 1996, vol. 2825, part two of two parts, pp. 812-821, a wavelet packet based compression scheme for single lead ECGs is disclosed, including QRS clustering and grouping of heart beats of similar structures. For each heart beat detected, its QRS complex is compared to templates of previously established groups. Point-by-point differences are used as similarity measures. The current beat is assigned to the group whose template is most similar, provided predetermined conditions are satisfied. Otherwise a new group is created with the current QRS complex used as the initial group template.

SUMMARY OF THE INVENTION

An object of the present invention is to provide a technique for separation of cardiac rhythms in a reliable way on the basis of electrogram event clustering The above object is achieved in accordance with the invention by an apparatus for analyzing cardiac events detected in electrogram (EGMs) having a feature extraction unit that derives features of the cardiac events for discriminating among different types of detected cardiac events, and a clustering unit that groups cardiac events with similar features into a cluster, defined by predetermined cluster features, wherein the feature extraction unit determines a feature vector that describes waveform characteristics of the cardiac event EGM signals by means of a wavelet transform, and wherein the clustering unit determines a distance or distances between the feature vector and corresponding cluster feature vectors in order to assign the cardiac event in question to the cluster that results in a minimum distance, as long as the minimum distance is less than a predetermined threshold value.

Certain arrhythmias are diagnosed immediately to give proper therapy, while, for others, it may be sufficient to record the rhythm for data collection purposes. Thus, the classification problem, viz. to label the rhythms based on clusters using clinical terms, may not always be necessary to implement.

In an embodiment of the apparatus according to the invention both morphologic and temporal data are considered for clustering. Morphologic features are efficiently extracted by use of the dyadic wavelet transform after which the events are grouped by a leader-follower clustering embodiment. The event detection problem, based on the same transform, is previously treated in Swedish patent application no. 0103562-5.

According to another advantageous embodiment of the apparatus according to the invention an integrator is provided to integrate said distance over a predetermined period of time. By integrating the distance over a period of time it is possible to distinguish irregular rhythms, like atrial fibrillation, from regular rhythms. The integral total distance in the case of atrial fibrillation will be high whereas regular rhythms will result in a lower total distance.

The invention also relates to a heart stimulator provided with the above-mentioned apparatus for controlling the therapeutic stimulation depending on arrhythmia detection.

DESCRIPTION OF THE PREFERRED EMBODIMENTS

P Wave Detection and Feature Extraction

Figure 1:
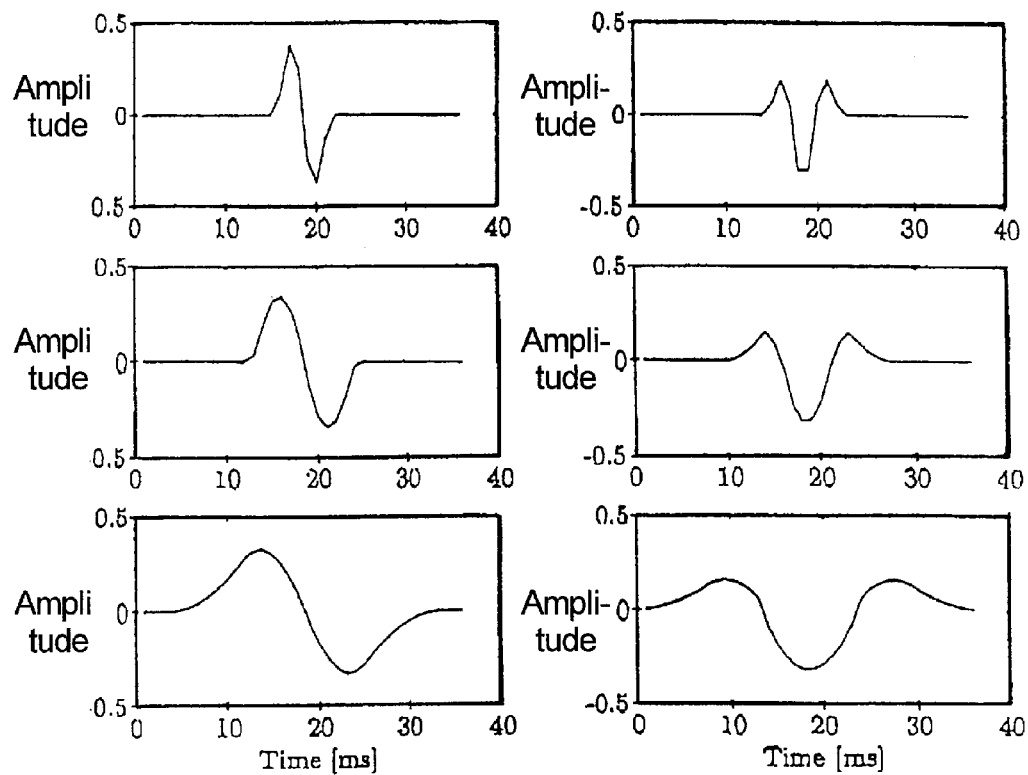
FIGS. 1a and 1b illustrate impulse responses of a filter bank used for cardiac event detection in accordance with the present invention.

A signal model assuming that the event waveform is composed of a linear combination of representative signals is considered. The feature extraction problem is then to estimate the individual components of the representative signals since each morphology will have its own linear combination. By using the dyadic wavelet transform, different widths of the two fundamental monophasic and biphasic waveforms are included in the model at a low cost.

Feature Extraction

It is assumed that the QRS waveform is composed of a linear combination of representative signals, $$H=[h_1 \ldots h_P] \tag{2}$$

where each function, $h_j$, $j=1, \ldots, P$, is of size M×1. The only restriction on H is that it must have full rank. Different morphologies, s(n), are modelled by the P×1 coefficient vector θ(n), with the linear model $$s(n)=H\theta(n) \tag{3}$$

where n is a temporal variable describing when the event occurs. The observed signal, x(n), is assumed to be modelled by, $$x(n)=H\theta(n)+w(n) \tag{4}$$

where the M×1 noise vector w(n) is assumed to be zero-mean, white, and Gaussian with variance $$\sigma_\omega^2.$$

Consequently, x(n) is defined as $$x(n) = \begin{bmatrix} x(n) \\ \vdots \\ x(n+M-1) \end{bmatrix} \tag{5}$$

implying an event duration of M samples, beginning at n. The probability density function x(n) for a specific realization of θ(n), p(x(n); θ(n)), is thus given by $$p(x(n); \theta(n)) = \frac{1}{\left(2\Pi\sigma_\omega^2\right)^{\frac{M}{2}}} \exp\left[-\frac{1}{2\sigma_\omega^2}(x(n)-H\theta(n))^T(x(n)-H\theta(n))\right] \tag{6}$$

In this model, a complete description of a QRS complex is provided by the deterministic unknown parameter vector θ(n). The absence of a QRS complex corresponds to the case when θ(n) is equal to 0, where 0 is the P×1 zero vector. In general, no a priori knowledge is available on θ(n), and therefore an estimate is required before detection can take place. Furthermore, only one event is assumed to take place within the observation interval $0 \leq n \leq N$.

Filterbank Representation

The descriptive functions in H have been selected such that the following three aspects have been taken into particular account:

1. the main morphologies of the QRS complex are mono- and/or biphasic
2. the broad range of QRS complex durations, and
3. a low complexity implementation.

The wavelet transform is particularly suitable since it is a local transform, i.e., it provides information about the local behaviour of a signal. One wavelet decomposition method which may be efficiently implemented is the dyadic wavelet transform. By careful selection of the filters, a suitable filter bank including mono-and biphasic impulse responses can be obtained. A symmetric lowpass filter, f(n), is used repeatedly in order to achieve proper frequency bands. This filter is combined with one of two filters, $g_b(n)$ or $g_m(n)$, which together define the waveform morphology (the subindices b and m denote bi- and monophasic, respectively). For the biphasic case, the recursion is expressed as, $$h_{1,b}(n) = g_b(n) \tag{7}$$
$$h_{2,b}(n) = f(n) * g_b(2n)$$
$$h_{3,b}(n) = f(n) * f(2n) * g_b(4n)$$
$$\vdots$$
$$h_{q_{max},b}(n) = f(n) * \ldots * \int (2^{q_{mas}-3} n) * g_b(2^{q_{max}-1} n)$$

in which the subindex $q_{max}$ represents the maximum (coarsest) scale.

It is now possible to present an expression for H which is composed of one biphasic and one monophasic part, $$H = [\tilde{H}_b \ \tilde{H}_m] \tag{8}$$

where the biphasic $H_b$ is defined as $$H_b = [h_{q_{min},b} \ \ldots \ h_{q_{max},b}] = \begin{bmatrix} h_{q_{min},b}(0) & \cdots & h_{q_{max},b}(0) \\ \vdots & \ddots & \vdots \\ h_{q_{min},b}(M-1) & \cdots & h_{q_{max},b}(M-1) \end{bmatrix} \tag{9}$$

where the subindex $q_{min}$ represents the minimum scale and $q_{min} < q_{max}$. The monophasic matrix $H_m$ is computed in a corresponding way. The reversed order of the columns in $\tilde{H}$, denoted with $\tilde{H}$ in (8), is introduced in order to be consistent with the model assumed in (4).

In order to mimic the desired mono- and biphasic waveforms with a low complexity filter bank structure, short filters with small integer coefficients were used. In (7), the impulse response f(n) was chosen as a third order binomial function, $$F(z) = (1 + z^{-1})^{L=2} 1 + 3z^{-1} + 3z^{-2} + z^{-3} \tag{10}$$

where F(z) is the Z-transform of f(n). For the biphasic filter bank, the filter $g_b(n)$ was selected as the first order difference, $$g_b(n) = [-1 \ 1] \tag{11}$$

The filter $g_m(n)$ was chosen such that a compromise between the requirement of a DC gain equal to zero and an approximately monophasic impulse response was achieved. A reduction of complexity results when $g_b(n)$ is reused, $$g_m(n) = g_b(n) * g_b(n) = [1 -2 \ 1] \tag{12}$$

For this particular choice of $g_m(n)$ and by using Mallat's algorithm, it is possible to calculate both the biphasic and the monophasic filter output from each scale by using f(n) once and $g_b(n)$ twice. The filter bank impulse responses are shown in FIGS. 1a and 1b. The filter bank includes two orthogonal signal sets where the width of the signal varies within each set. In FIG. 1a, $h_{j,b}$ (n) is shown for j=2, . . . ,4 from top to bottom, and in FIG. 1b, the corresponding $h_{j,m}(n)$ are shown.

ML Parameter Estimation

The unknown coefficient vector θ(n) can be estimated by using the maximum likelihood criterion according to, $$\hat{\theta}(n) = \arg\max_{\theta(n)} p(x(n); \theta(n)) \tag{13}$$

However, $\hat{\theta}(n)$ is only of interest for those n for which the probability of an event, or, equivalently, for which the likelihood ratio test function T(x(n)) is maximized, $$\hat{n} = \arg\max_{n} T(x(n)) \tag{14}$$

For this case, T (x(n)) can be shown to be [14], $$T(x(n)) = x(n)^T H(H^T H)^{-1} H^T x(n) \tag{15}$$

for the case when $\sigma_\omega^2$ is assumed to be constant.

The optimal estimate $\hat{\theta}$ for the detected event at $\hat{n}$ is thus expressed as $$\hat{\theta} = \arg\max_{\theta(\hat{n})} p(x(\hat{n}); \theta(\hat{n})) \tag{16}$$

The MLE of $\theta(\hat{n})(n)$ is found by maximizing $p(x(\hat{n});\theta(\hat{n}))$, or equivalently minimizing the MSE, $$(x(\hat{n})-H\theta(\hat{n}))^T(x(\hat{n})-H\theta(\hat{n}))=x(\hat{n})^T x(\hat{n})+\theta(\hat{n})^T H^T H\theta(\hat{n})-2\theta(\hat{n})^T H^T x(\hat{n}) \tag{17}$$

Derivation with respect to $x(\hat{n})$ yields the optimum θ, $$\hat{\theta}(\hat{n}) = (H^T H)^{-1} H^T x(\hat{n}) = (H^T H)^{-1} H^T x(\hat{n}) \tag{18}$$

By using the above formulation, it is also possible to derive a generalized likelihood ratiodetector based on (15).

Rate

The central parameter for classification of cardiac arrhythmias is the heart rate. Most arrhythmias are defined in terms of heart rate, although sometimes with rather fuzzy limits. Consequently, rate should be considered in order to improve performance. The RR interval, $\Delta t$, is defined as the duration between two consecutive events, $$\Delta t_k = (\hat{n}_k - \hat{n}_{k-1}) T_S \tag{19}$$

where $\hat{n}_k$ and $\hat{n}_{k-1}$ denote the occurrence times of the events, and $T_S$ denotes the sampling period.

Leader-Follower Clustering

The choice of leader-follower clustering is based on a number of features which makes it suitable for the present invention, viz.
  on-line processing (non-iterative), and
  self-learning, i.e., no a priori knowledge of the of clusters is needed.

The starting point is the assumption that an event is present for which it should be decided whether it belongs to an already existing cluster or if a new cluster should be initiated. Since, no knowledge is a priori available on which rhythms or morphologies to be expected, the chosen algorithm must be self-learning. The leader-follower clustering algorithm is constituted by four quantities:
  1. The event parameter vector, $\phi(n_k)$, containing the features of the k:th event that occurs at time $n_k$.
  2. The cluster center $\mu_i$, and the covariance matrix $\Sigma_i$; that together define the i:th cluster. Since both $\mu_i$ and $\Sigma_i$ are unknown, they are replaced by their estimates $\hat{\mu}_i$ and $\hat{\Sigma}_i$; respectivey.
  3. The metric, $d_i^2$, determine the distance between $\phi(n_k)$ and $\mu_i$; according to some suitable function.
  4. A rule for adaptation of the cluster parameters for the winning cluster.

Initialization of New Clusters

During run-time, a finite number of clusters exists which represent the rhythms having appeared until present time. Thus, it is occasionally necessary to initialize a new cluster when the existing ones do not sufficiently well fit the present event. When the distance function $d_j^2$ exceeds a certain threshold, $\eta$, it is more likely that the event belongs to a new cluster than to any of the existing clusters. The selection of $\eta$ is a tradeoff between cluster size and cluster resolution in the sense that choosing a small $\eta$ will result in many clusters with few clustering errors. On the other hand, a large $\eta$ results in few clusters but in more errors.

The minimum distance between $\phi(n)$ and $\mu_i$; with respect to both i and n is $$d_{\min}^2 = \min_{i,l} d_i^2(l) \quad i=l, \ldots, I \; l = \hat{n}_k - \frac{K}{2}, \ldots, \hat{n}_k + \frac{K}{2} \tag{20}$$

over the search interval K. The corresponding minimum distance indices are found as $$[i_{\min}, n_{\min}] = \arg\min_{i,l} d_j^2(l) \tag{21}$$

The decision rule based on the comparison of $d_{min}^2$ and $\eta$ is expressed as $$d_{\min^2} \begin{cases} \rangle\eta: & \text{Initialize new cluster} \\ \langle\eta: & \text{Assign to winning cluster} \\ \langle\rho\eta: & \text{Update winning cluster} \end{cases} \tag{22}$$

where $0 < p < 1$. When the upper relation in (22) holds, a new cluster is initialized by first increasing the number of clusters by one, $I = I+1$, given that $I < I_{max}$ where $I_{max}$ is the maximum number of clusters, and then initializing the new cluster as, $$\hat{\mu}_I = \Phi(\hat{n}_k) \tag{23}$$

On the other hand, if $I = I_{max}$ the algorithm needs to discard one of the existing clusters. This can be done by elimination of, e.g., the oldest or the "smallest" cluster. By the term "smallest" cluster is meant that cluster which most rarely is fitted with a detected cardiac event.

For the middle and lower conditions in (22), the existing minimum distance cluster $i_{min}$ is selected as the winning cluster. However, only the lower condition results in a cluster parameter update. The reason for including such a distinction is that only closely similar events should be used for cluster updates in order to reduce contamination.

Mahalanobis Distance Function

The distance between the feature vector $\theta(n)$ and each cluster $\hat{\mu}_1$, is defined as the Mahalanobis distance, which is a normalized Euclidean distance in the sense that it projects the parameter vector elements onto univariate dimensions by including the inverse covariance matrix $\Sigma_i^{-1}$. Thus, a feature with a larger variance in $\phi(n)$ will be assigned a larger share of the hyperspace before normalization compared to that with a lower variance. A consequence of normalization is that the Mahalanobis distance works well on correlated data since $\Sigma_i^{-1}$ then acts as a decorrelator.

When searching for the minimum distance, a grid search over n is performed. This grid search is necessary since it not only minimizes the distance but also results in a more accurate fiducial point estimate than what would be the case when only considering $T(x(\hat{n}_k))$. The minimum distance is thus found by a grid search with respect to all existing clusters, $i = 1, \ldots, I$, and all feature vectors within the duration of an event I as defined in (20), $$d_i^2(l) = (\Phi(l) - \hat{\mu}_i)^T \hat{\Sigma}_i^{-1} (\Phi(l) - \hat{\mu}_i) \tag{24}$$

Reference Feature Adaptation

In order to track changes in the features of the different rhythms, adaptation of both $\hat{\mu}_{i\;min}(k)$ and $$\hat{\Sigma}_{i\;min}^{-1}(k)$$

are desirable, here the event index k has been included for clarity. For $\hat{\mu}_{i_{min}}(k)$, an exponentially updated average is used:

$$\hat{\mu}_{i_{min}}(k) = \hat{\mu}_{i_{min}}(k-1) + \gamma\epsilon(k) \tag{25}$$

where $$\epsilon(k) = \Phi(\hat{n}_{min}) - \hat{\mu}_{i_{om}}(k-1) \quad (26)$$

The exponential update factor γ is confined to the interval 0<γ<1.

The inverse covariance matrix, $$\hat{\Sigma}_{i\,min}^{-1}(k),$$

is estimated by exponential averaging of the new cluster difference matrix $\epsilon(k)\epsilon^T(k)$ using the update factor $(1-\alpha)$, $$\hat{\Sigma}_{i_{min}}^{-1}(k) = \left((\alpha)\hat{\Sigma}_{i_{min}}(k-1) + (1-\alpha)\varepsilon(k)\varepsilon^T(k)\right)^{-1} \quad (27)$$

Using the matrix inversion lemma $$A = B^{-1} + CD^{-1}C^T \quad (28)$$

$$A^{-1} = B - BC(D + C^TBC)^{-1}C^TB \quad (29)$$

and pairing the terms in (27) with the ones in (28), $$A = \hat{\Sigma}_{imin}(k) \quad (30)$$

$$B^{-1}\alpha\hat{\Sigma}_{imin}(k-1) \quad (31)$$

$$C = \epsilon(k) \quad (32)$$

$$D^{-1} = (1-\alpha) \quad (33)$$

The inverse $\hat{\Sigma}_{i\,min}^{-1}(k-1)$ in (27) may be computed without any matrix inversions as, $$\hat{\Sigma}_{i_{min}}^{-1}(k) = \alpha^{-1}\hat{\Sigma}_{i_{min}}^{-1}(k-1) - \frac{\alpha^{-1}\hat{\Sigma}_{i_{min}}^{-1}(k-1)\varepsilon(k)\varepsilon^T(k)\alpha^{-1}\hat{\Sigma}_{i_{min}}^{-1}(k-1)}{(1-\alpha)^{-1} + \varepsilon^T(k)\alpha^{-1}\hat{\Sigma}_{i_{min}}^{-1}(k-1)\varepsilon(k)} \quad (34)$$

By utilizing the matrix inversion lemma, the computational complexity of the operation is reduced from $O(P^3)$ to $O(P^2)$.

Algorithm Initialization

In leader-follower clustering, clusters are initialized as they become needed. This feature is convenient since it does not automatically introduce any unused clusters. However, it also puts demands on the algorithm to be able to create new clusters when necessary, and also to terminate clusters either not used for long or with only a few events. Initially, the total number of clusters, I, is equal to one. The algorithm is initialized by assigning the parameter vector $\Phi(\hat{n}_i)$, which maximizes the test statistic in (14) of the first event, to the first cluster, cf. (23), $$\hat{\mu}_1 = \Phi(\hat{n}_1) \quad (35)$$

For the general case, $\Phi(\hat{n}_k)$ is composed of a subset of the representative functions together with the preceding RR-interval, $$\Phi(\hat{n}_k) = \begin{bmatrix} \hat{\theta}_s(\hat{n}_k) \\ \|\hat{\theta}_s(\hat{n}_k)\| \\ \Delta t_k \end{bmatrix} \quad (36)$$

where $\hat{\theta}_s(\hat{\pi}_k)$ is a subset of the most discriminating elements in $\hat{\theta}_s(\hat{\pi}_k)$.

It should be noted that an event is defined by its depolarization wave. Consequently, Δt is not included in the arrival time estimation of $\hat{n}_k$, but instead computed afterwards. The time continuous notation of $\Delta t_k$ is preferred since it results in a suitable magnitude similar to the normalized morphological information in $\theta_s$.

Figure 2:
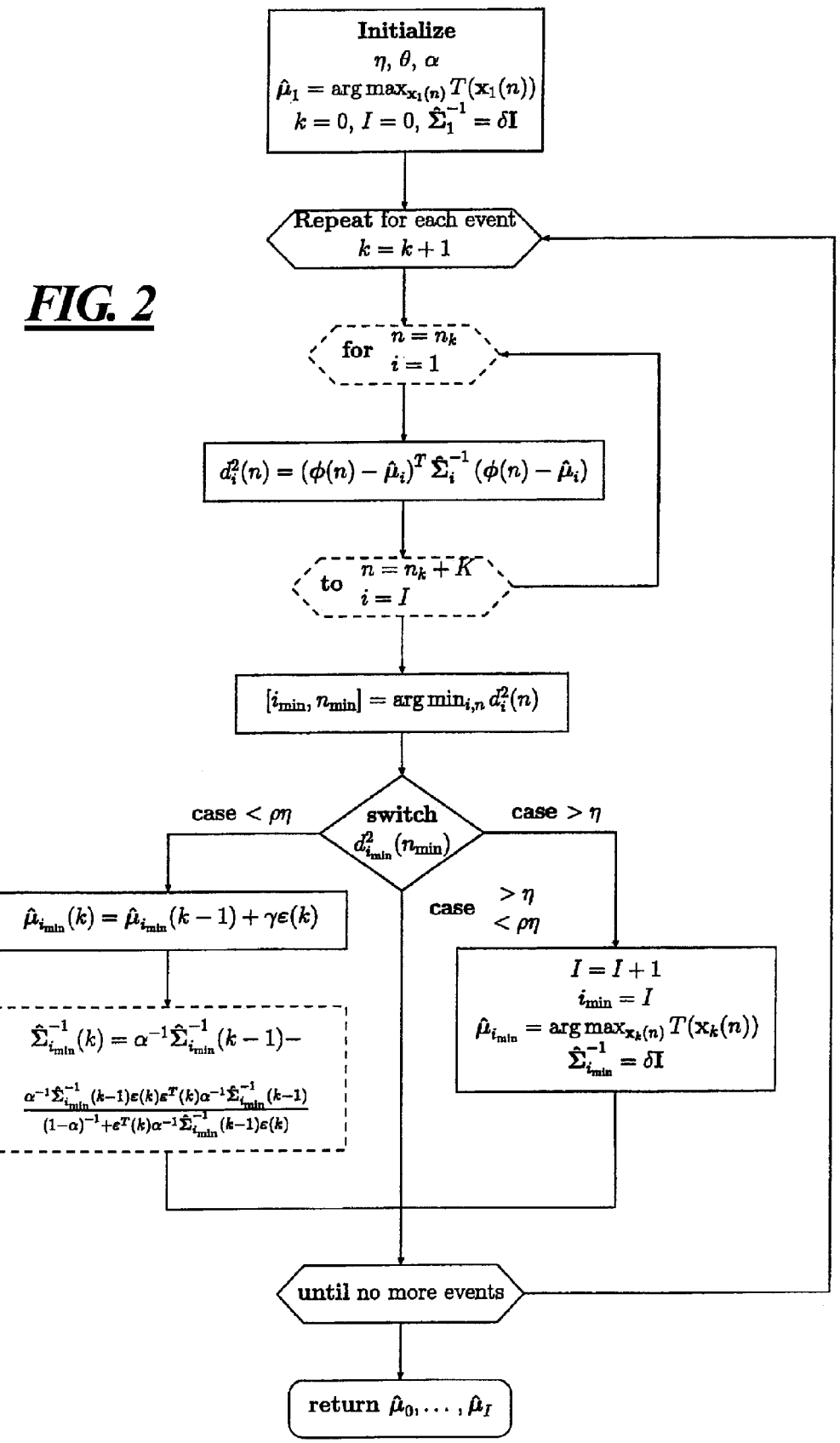
FIG. 2 is a flow chart of a clustering algorithm performed in the apparatus according to the present invention.

The inverse correlation matrix estimate is initialized in the same way for all clusters; a simple solution is to set it equal to a scaling of the identity matrix I, $$\hat{\Sigma}_i^{-1} = \delta I \quad (37)$$

where σ is a design parameter. The complete clustering algorithm for organized events is presented in the flow chart in FIG. 2.

Reduced-Complexity Clustering

In order to develop a more efficient algorithm in terms of performance versus power consumption and to evaluate the power consumption itself, a simple measure of the computational complexity can be used, namely, the total number of multiplications. This quantity represents a much more complex operation than do additions. In this algorithm, where most operations are of the nature "multiply-accumulate", the number of additions is of the same order as the number of multiplications and may thus be neglected without significant loss of accuracy.

In order to reduce the computational complexity, focus is put on reducing the number of multiplications. The dominant contributions of multiplication operations are found in (24) and (34) which require P(P+1) and P/2 (3P+5) multiplications, respectively, considering certain symmetry properties of $$\hat{\Sigma}_i^{-1}.$$

Furthermore, one division is required in (34). However, according to (20), (24) is performed IK times per event while (34) is performed only once per event.

Based on the above performance figures, a few approximations can be identified:

to use only the peak(s) in $T(x(\hat{n}))$ instead of a complete grid search, to use a simplified $$\hat{\Sigma}_i^{-1},$$

and to use a likelihood based search sequence over the clusters, i.e., to start with the most likely cluster and to stop the search if a sufficiently small distance is found.

Simplifying the grid search from spanning both samples and clusters in (20) to span over only clusters, $$d_{min}^2 = \min_i d_i^2(\hat{n}) \quad (38)$$

the number of multiplications may be reduced by a factor K to IP(P+1). Due to sensitivity in $T(x(\hat{n}))$, the feature vectors resulting in the peaks for two different events may differ significantly, this simplification is likely to result in more clusters. A useful compromise may instead be to use the coefficients from, e.g., the 3 largest peaks in $T(x(\hat{n}))$ resulting in 3IP(P+1) multiplications per event.

Since a cardiac event lasts for longer time than one sample those samples which give the filter coefficients which are most similar to the cluster reference are determined. A grid search over 40 msec is preferably made. In this way coefficients of greatest importance locally are determined. For this decision $T(x(n))$ is considered and samples generating a peak are chosen, i.e. $T(x(n-1))<T(x(n))>T(x(n+1))$, since they indicate the probability for the presence of an event.

Another simplification, based on the approximation of orthogonality between the different wavelet scales as well as the RR interval, is to simplify $$\hat{\Sigma}_i^{-1}$$

by only including its diagonal elements in the adaptation, $$\hat{\Sigma}_{i_{min}}^{-1} \approx \alpha^{-1} \hat{\Sigma}_{i_{min}}^{-1} + (I - \alpha)\mathrm{diag}(\varepsilon(k)\varepsilon^T(k)) \quad (39)$$

where diag(A) returns the diagonal elements of the square matrix A. By using this approximation, the number of multiplications used for the estimation of $$\hat{\Sigma}_i^{-1}$$

is reduced to 3P. Additionally, the distance computation in (20) is simplified and may be reduced to 2IKP multiplications per event.

A reasonable assumption is often that successive events originate from the same rhythms. Considering this knowledge, it would be sufficient to compute the distances for the previously selected cluster. In doing so, the number of multiplications in (38) are reduced even further.

Table 1 presents the different detector versions as defined by their distinguishing features and shows computational complexity for the different versions of the clustering algorithm.

| | Features 1 | | |
|---|---|---|---|
| Version | $\hat{\Sigma}_{i\,min}^{-1}$ | Search alg. | Complexity C |
| A | Full | Interval | $IKP(P+1) + \frac{P}{2}(3P+5)$ |
| B | Diagonal | Interval | $2IKP + 3P$ |
| C | Full | 3 peak | $3IP(P+1) + \frac{P}{2}(3P+5)$ |
| D | Diagonal | 3 peak | $6IP + 3P$ |

Figure 3A:
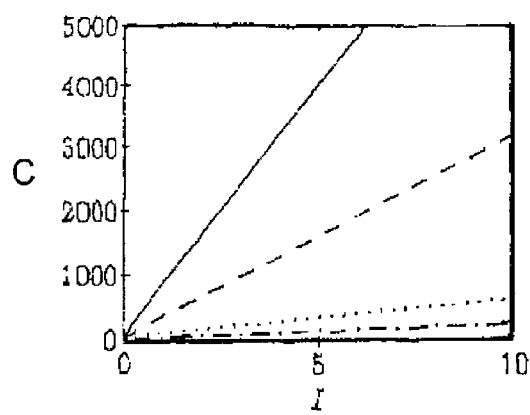
FIGS. 3a and 3b illustrate the computational complexity for different clustering algorithms.
Figure 3B:
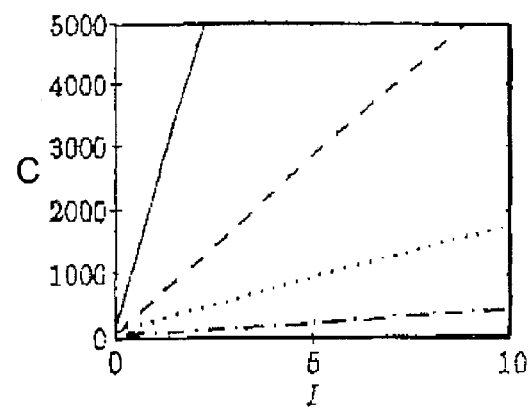

The total computational complexity, C, as reflected by the number of multiplications for the different algorithm versions, is presented in FIG. 3 as a function of 1. In FIG. 3 the solid line shows an algorithm version A, dashed line a version B, dotted line a version C, and a version D by dash-dotted line), for a feature vector with (a), P=4, and (b), P=7 elements.

Results

The results are obtained by studying the performance of the following quantities:
algorithm versions, as presented in Table 1, and
noise tolerance, for noise-free signals and for signals with background noise of 50 μV RMS.

The following parameter settings have been used (unless otherwise stated), $$\alpha=1.05 \; \gamma=0.025 \; \delta=50 \; K=40 \quad (49)$$

It is noted that $\alpha^{-1}$ is chosen to offer faster adaption than γ. The reason for that is that the initial estimate $$\hat{\Sigma}_i^{-1}$$

is likely to be less accurate than the initial estimate $\hat{\mu}_i$. Also, δ is chosen to have the same order of magnitude as the steady state eigenvalues $$\hat{\Sigma}_i^{-1}.$$

It should be noted that the different algorithm versions are not fully comparable in terms of performance for a specific η due to the differences in distance computation. In versions B and D, where a diagonal $$\hat{\Sigma}_{i_{min}}^{-1}$$

is used, the lack of non-diagonal information results in a nonorthogonal distance which is larger than the orthogonal one. Since versions C and D make use of a limited search, the minimum distance found may differ from the global minimum distance for the event. Both these algorithmic differences imply an increase in clustering quality for a certain value of η, however, at the expense of more introduced clusters.

Evaluation Measures

The two main quantities evaluated are clustering performance and computational complexity, see FIG. 3; these two quantities are in general conflicting. In the evaluation, a cluster is assigned to that cardiac rhythm which contains the most events in the cluster. This rhythm is denoted as the dominant rhythm within the cluster. With respect to the dominant rhythm, the cluster is defined as a correct cluster, whereas it is erroneous to all other rhythms. If a rhythm is found to be dominant in more than one cluster, such clusters are first merged in the performance evaluation. The number of events in the correct cluster which belongs to the i:th dominant rhythm is equal to $N_D(i)$, while the number of events belonging to any other false rhythm in the cluster is equal to $N_F(i)$. The number of events of the dominant rhythm which are not classified in a correct cluster, i.e., missing, is equal to $N_M(i)$.

The performance of the algorithm is evaluated in terms of probability of a correct clustering of an event, $P_{CC}(i)$, and probability of a dominant event in a cluster, $P_{DE}(i)$. The first parameter is expressed as the share of correctly clustered events within a rhythm and is, using the above parameters, defined by $$P_{CC}(i) = \frac{N_D(i)}{N_D(i) + N_M(i)} \quad (41)$$

The second parameter may be expressed as the share of dominant rhythm events within a cluster, and is defined as $$P_{DE}(i) = \frac{N_D(i)}{N_D(i) + N_M(i)} \quad (42)$$

For the case when a rhythm completely lacks a correct cluster, $P_{DE}(i)$ is undefined; the rhythm is then excluded from subsequent statistical computations. Averaging $P_{CC}(i)$ and $P_{DE}(i)$ over all clusters results in the global performance measures $P_{CC}$ and $P_{DE}$, respectively.

It should be pointed out that $P_{CC}(i)$ and $P_{DE}(i)$ reach their maximal value of 1 when η is sufficiently small such that the number of clusters equals the total number of beats evaluated. This is, of course, a highly undesirable solution although performance, as expressed in (41) and (42), will be excellent. For this reason, the total number of clusters, I, is a crucial parameter to be considered. Here, the average Ī is used together with the minimum and maximum number of clusters for a case, $I_{min}$ and $I_{max}$, respectively.

The power consumption of the algorithm is an important parameter which determines the pacemaker life span. In this study, power consumption is approximated by the computational complexity defined above as the total number of multiplications. As shown, the computational complexity depends mainly on three parameters: the feature vector length, P, the search interval, K and the cluster size, I.

Noise-Free Signal Clustering Performance

Figure 4A:
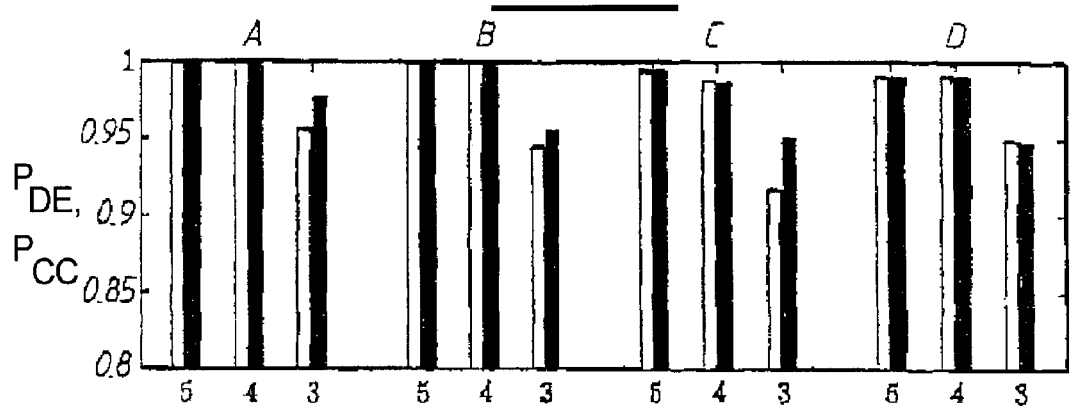
FIG. 4a illustrates clustering performance in terms of probability for correct clustering of an event, as well as the probability of a dominant event in the cluster.
Figure 4B:
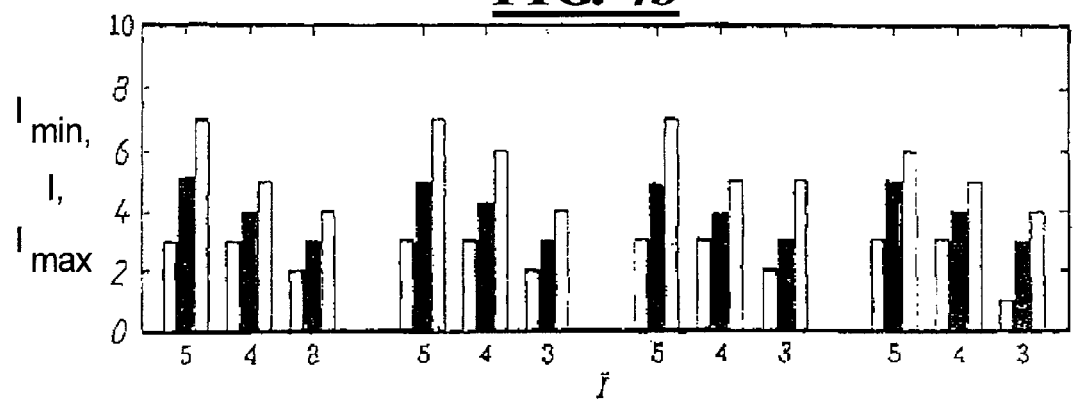
FIG. 4b illustrates a histogram spread of the number of clusters.

FIGS. 4a and 4g illustrate clustering performance in terms of $P_{DE}$ and $P_{CC}$, see FIG. 4a, and $I_{min}$, Ī and $I_{max}$, see FIG. 4 (b). Thus in FIG. 4a clustering performance is shown as depending on Ī for $P_{CC}$ (dark bars) and $P_{DE}$ (bright bars) for noise-free signals. In FIG. 4b, the spread between the different cases is shown as, from left to right, $I_{min}$, Ī and $I_{max}$.

The presented algorithm versions are found in Table 1 and three values of Ī have been chosen for comparison; 3, 4 and 5. Versions A and B perform similarly for all three cases, and achieve $P_{DE}=1$ and $P_{CC}=1$ for Ī=4 and Ī=5, respectively, by creating an acceptable number of clusters. However, it can be seen from FIG. 4b that a large difference in the number of initialized clusters between different cases is present. For version B, a slight increase in both Ī and $I_{max}$ is observed for Ī=4. However, this increase is more due to an unfortunate step-like behaviour in the results for the given Ī than for any significant decrease in performance. The values of η used in FIGS. 4a and 4b for the different versions are shown in Table 2.

TABLE 2

Values of η used in FIG. 4.

| Ī | Algorithm version | | | |
|---|---|---|---|---|
| | A | B | C | D |
| 5 | 3.6 | 4.2 | 5.4 | 5.8 |
| 4 | 4.6 | 4.8 | 7.0 | 7.2 |
| 3 | 9.6 | 9.6 | 12.0 | 10.8 |

Versions C and D perform slightly worse than do versions A and B. Contrary to the latter ones, neither version achieves $P_{DE}=1$ or $P_{CC}=1$ for the presented Ī, see FIG. 4a.

Figure 5A:
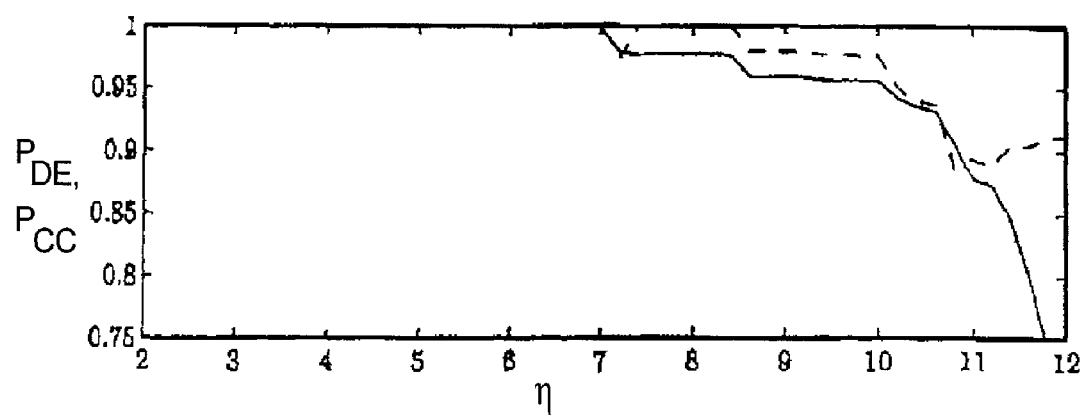
FIG. 5a illustrates clustering performance as a function of a distance threshold.

FIG. 5a shows the clustering performance for version A in detail and its dependence on η. The most noteworthy result is that both $P_{DE}=1$ and $P_{CC}=1$ for η<7. It is also clear that clustering performance deteriorates rapidly for η>10. The increase in $P_{CC}$ for very high values of η is due to that not all rhythms are allocated to a dominant cluster and are therefore disregarded in the performance computation.

Figure 5B:
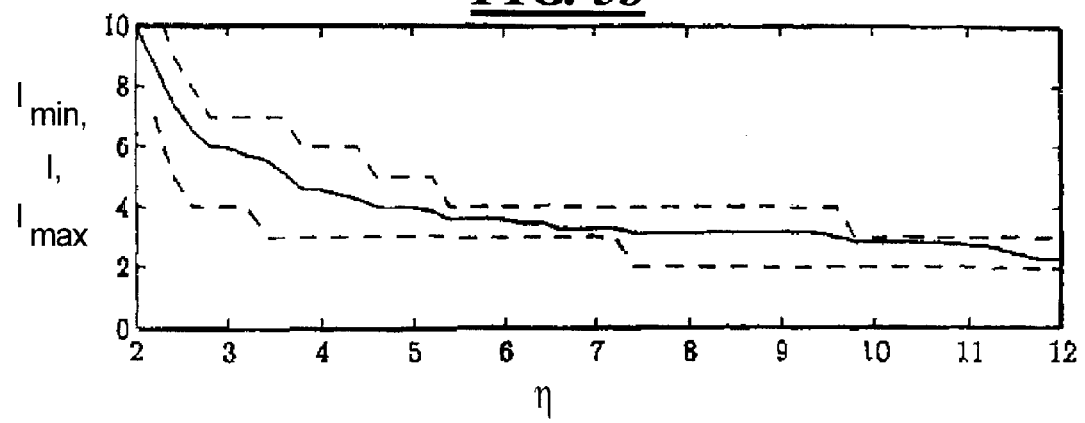
FIG. 5b illustrates the number of clusters as a function of the distance threshold.

In FIG. 5b, $I_{min}$, Ī and $I_{max}$ are presented as a function of the clustering threshold. Thus FIG. 5a shows clustering performance in terms of $P_{DE}$ (solid line) and $P_{CC}$ (dashed line) as a function of η for noise-free signals, and FIG. 5(b) the corresponding $I_{min}$, Ī and $I_{max}$. For η<3, the number of initiated clusters increases rapidly with decreasing rI. Within the interval 3<η<7, all rhythms initiate at least one cluster, while for η>7, this is not true for all cases. Removing the "worst case", the above is true for the other cases for η<10.

Figure 6:
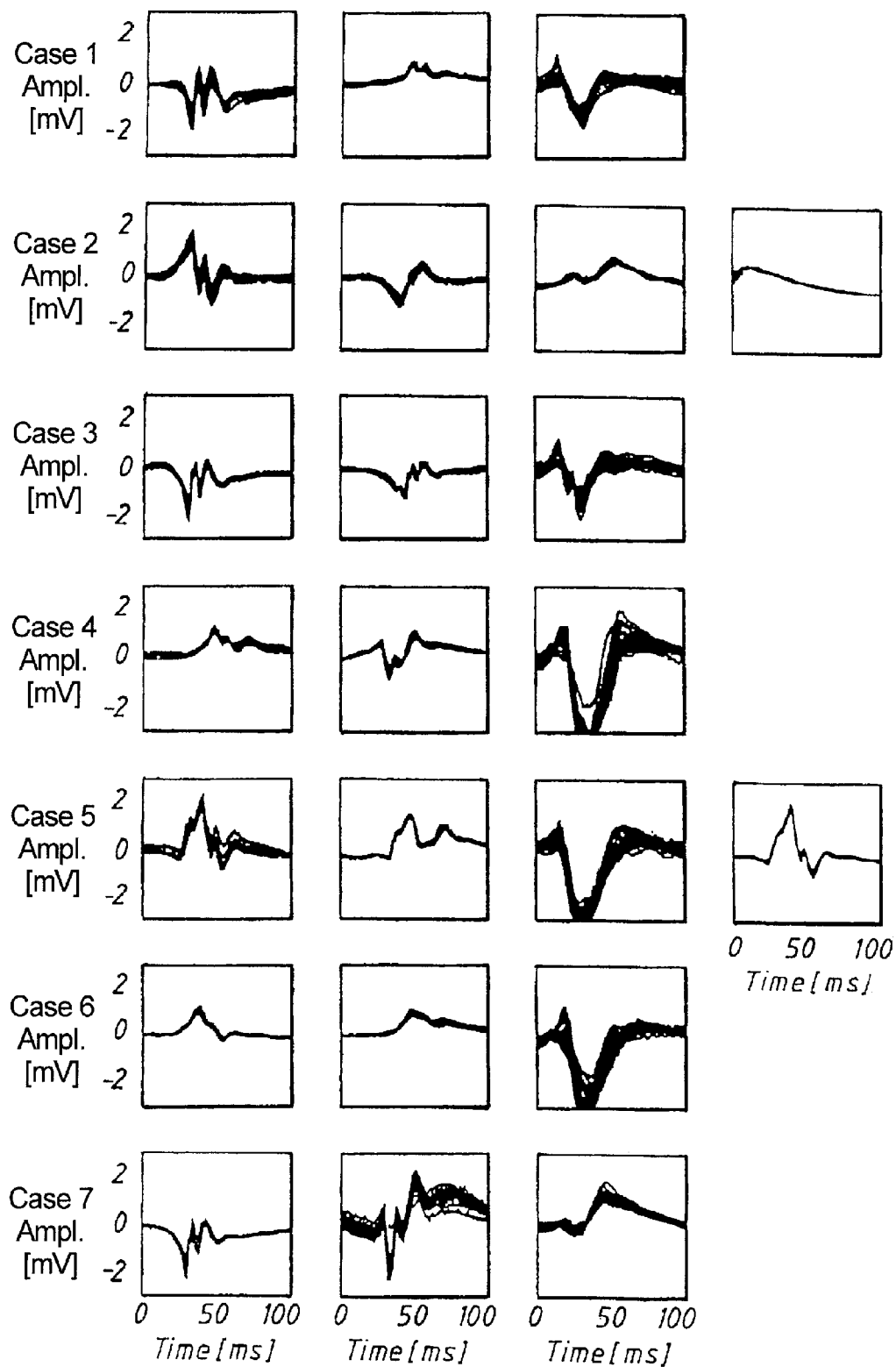
FIG. 6 illustrates the clustering performance for one set of parameters.

The clustering performance is exemplified for one set of parameters in FIG. 6 using η=7. Correct clustering with minimal number of clusters is achieved for two cases while an extra cluster is initialized for two cases. The reason for the extra cluster is that, for case 2, the temporal search interval is chosen too small for the third morphology from the left resulting in an extra cluster. For case 5 an actual difference in morphologies both on the up and down slopes of the dominant peak is discernible between the first and fourth clusters from the left.

Figure 7A:
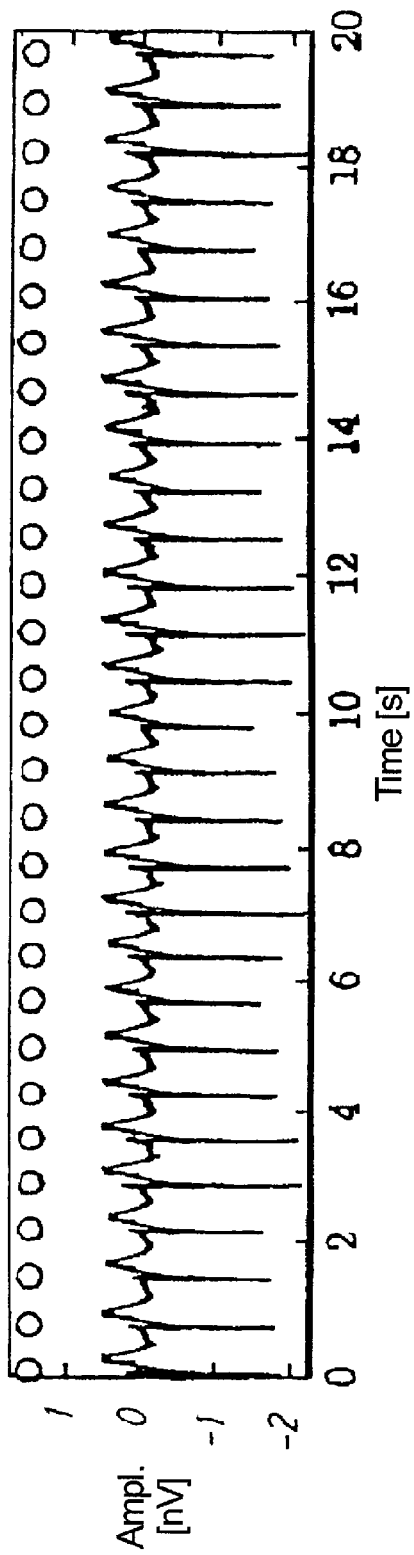
FIGS. 7a and 7b are examples of the clustering result for a connected EGM for three cases.
Figure 7B:
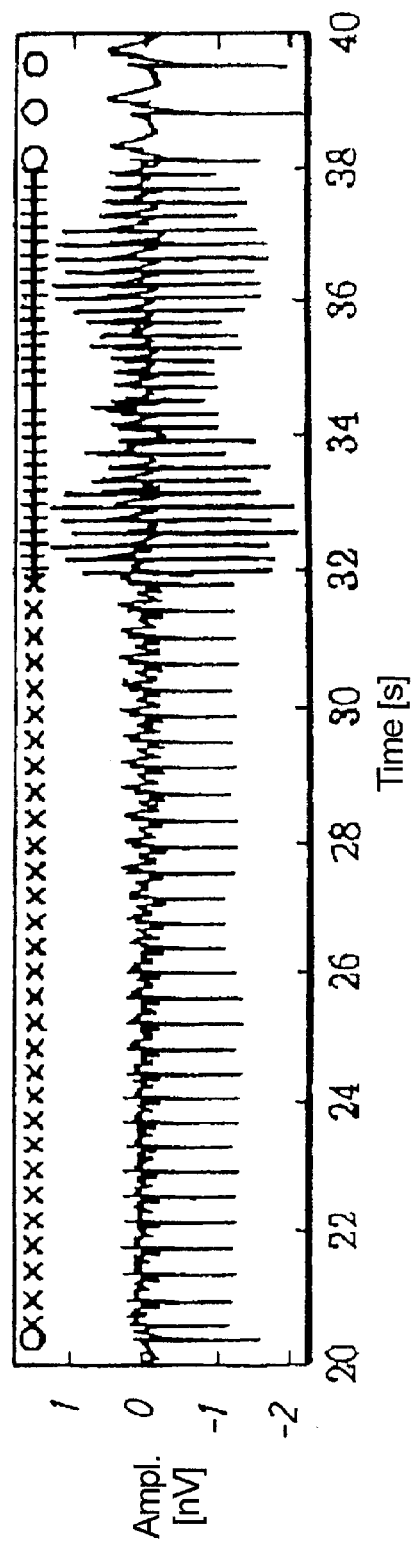

Clustering for a concatenated electrogram is presented for case 3 in FIG. 7, where three distinct rhythm classes can be discerned, viz. normal sinus rhythm followed by supraventricular tachycardia and atrial flutter. The EGM is shown together with the clusters, represented by o, x and +, respectively, assigned for each event. The different rhythms result in three clusters.

Figure 8:
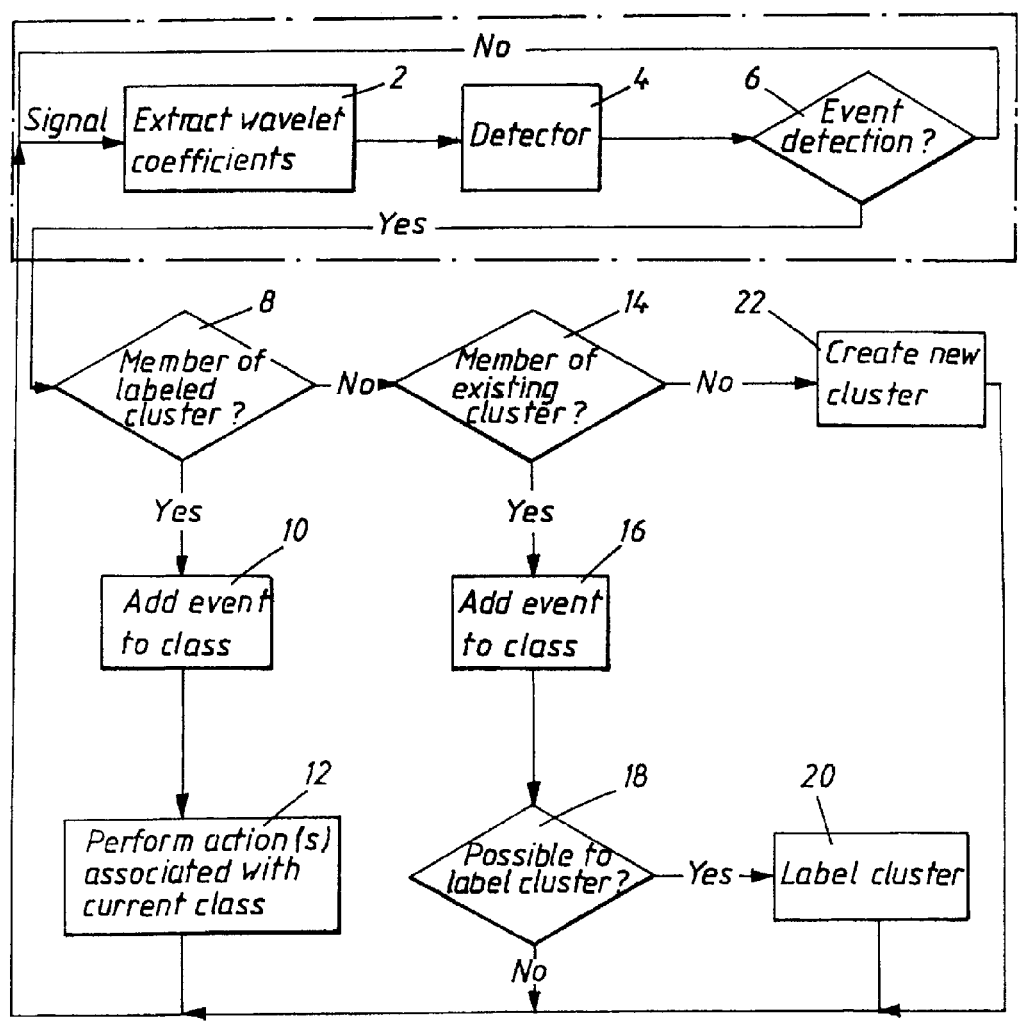
FIG. 8 is a flowchart describing the general functioning of an embodiment of an apparatus according to the invention.

FIG. 8 is a flow chart illustrating the function in broad outline of an embodiment of the apparatus according to the invention. At block 2 cardiac event features are extracted in the form of wavelet coefficients, and the event is detected, at 4, 6. At block 8 is checked whether the detected event is member of a labelled cluster. If so, the event is added to a class, at 10, and actions associated with that class are performed, at 12.

If the event is not member of a labelled class it is checked if it is a member of an existing cluster, at 14. If so, the event is added to a class, at 16, and it is checked if it is possible to label the cluster, 18, and if so the cluster is labelled, at 20.

If the event is not a member of an existing cluster, block 14, a new cluster is created as described above fitted to the detected cardiac event, at 22.

Thus according to the invention clustering events in the EGM is performed for use in implantable CRM devices, like heart stimulators. The invention is based on feature extraction in the wavelet domain whereupon the features are clustered based on the Mahalanobis distance criterion. According to advantageous embodiments of the apparatus according to the invention simplifications of the technique is proposed in order to reduce computational complexity to obtain a more implementationally feasible solution.

If the apparatus according to the invention is to be used for longer periods of data analysis, large clusters, although old, may be desirable to be kept in some way, while the oldest cluster may be selected to be removed if the application is based on shorter time frames. Also, due to the short data lengths, testing of such algorithms would be of limited value.

By combining detector/clusterer with labelling rules of a classifier a complete detector/classifier is obtained with the possibility to more accurate therapy.

The labelling need not be done in real time and probably more than one event will be needed to label a cluster. Once the cluster has been labelled using clinical terms, the actions associated with the particular class will be carried out immediately, i.e. in real time. Thus, the rules needed to label the cluster are not used in identifying the event itself.

The rules used to label the clusters are based on characteristics of the different possible events. Instead of the exact rules, the characteristics are consequently described.

Figure 9:
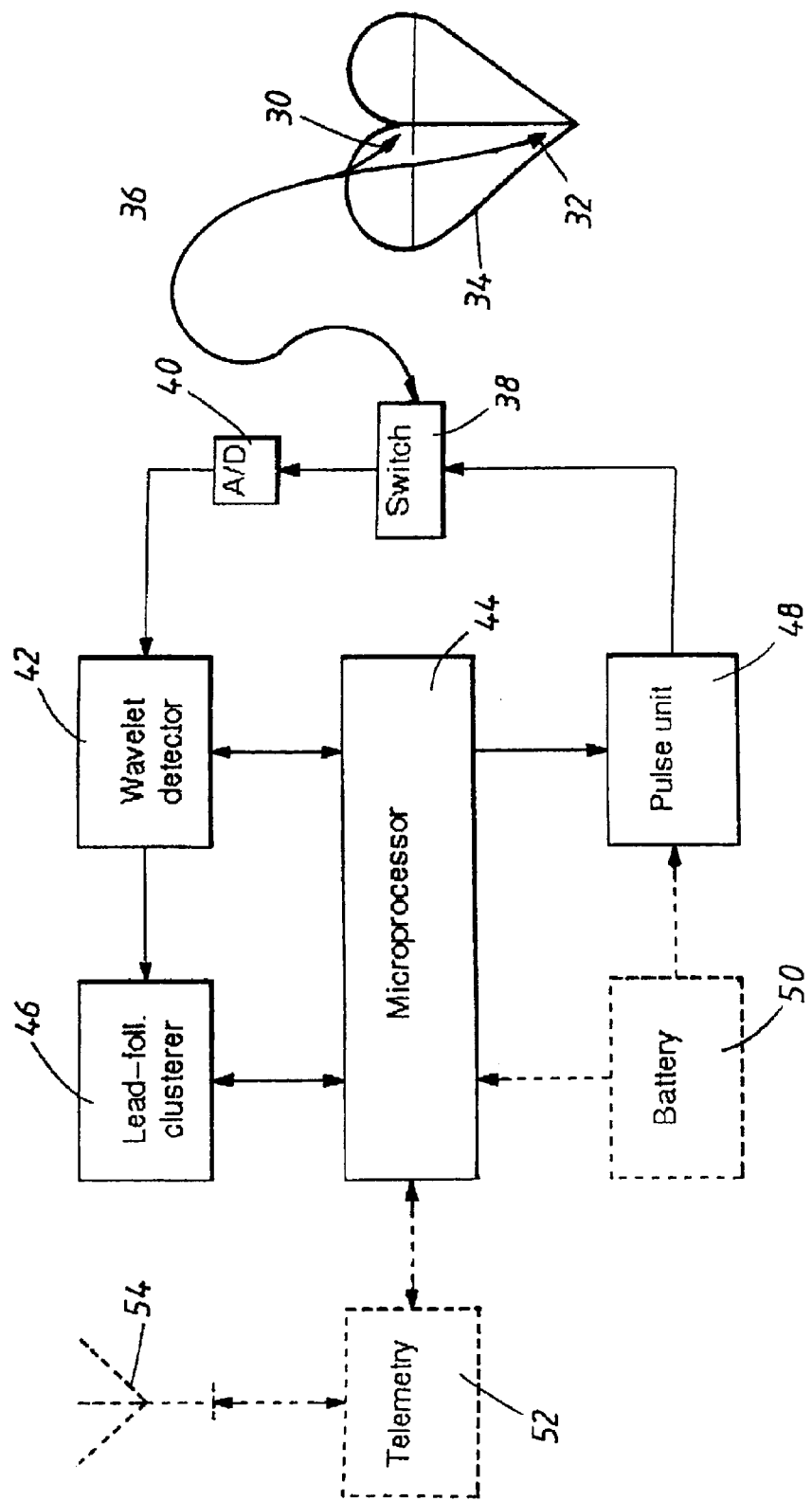
FIG. 9 is a block diagram of a heart stimulator providing with a cardiac event detecting apparatus in accordance with the present invention.

FIG. 9 is a block diagram of an embodiment of an implantable heart stimulator provided with the apparatus according to the invention. Electrodes 30, 32 implanted in the heart 34 of a patient are connected by a lead 36 to an A/D converter 40, via a switch 38 serving as overvoltage protection for the A/D converter 40. In the A/D converter 40 the signal is A/D converted and the digital signal is supplied to a wavelet detector 42.

The detector 42 decides whether a cardiac event is present or not as described earlier. Wavelet coefficients are calculated as well. Parameters of the detector 42 are programmable from the stimulator microprocessor 44. At the detection the coefficients and the RR information are forwarded to the clusterer 46 in which it is determined to which cluster the detected cardiac event belongs, as described previously. The clusterer 46 is preferably of a leader-follower type and also the cluster parameters are programmable from the microprocessor 44.

By the microprocessor 44 suitable therapy is decided depending on assigned cluster for the detected event and possible a priori knowledge about arrhythmia associated with the cluster in question. Thus it is possible to distinguish e.g. ventricular tachycardia from a sinus tachycardia by comparing the parameters with a known normal sinus rhythm. Parameters of the sinus tachycardia are then supposed to be similar to those of a normal sinus rhythm, whereas parameters of ventricular tachycardia differ significantly.

As an alternative the decision rules can be trained from a number of rhythms and the resulting rules are then used on test data, see Weichao Xu et al., "New Bayesian Discriminator for Detection of Atrial Tachyarrhythmias", DOI: 10.1161/01.CIR.0000012349.14270.54, pp. 1472-1479, January 2002. It is then possible to decide that a certain position of the cluster indicates e.g. a sinus rhythm, etc. Also this technique can be based on analysis of the feature vector for a cluster, and it is possible to decide if the beat is broad or narrow, large or small, or if the rhythm is regular or irregular.

The stimulator in FIG. 9 also includes a pulse unit 48 with associated battery 50 for delivery of stimulation pulses to the patient's heart 34 depending on the clustering evaluation.

The implantable stimulator shown in FIG. 9 includes telemetry means 52 with antenna 54 for communication with external equipment, like a programmer.

Although modifications and changes may be suggested by those skilled in the art, it is the intention of the inventor to embody within the patent warranted hereon all changes and modifications as reasonably and properly come within the scope of his contribution to the art.

We claim as our invention:

1. An apparatus for analyzing cardiac events, comprising:
   a feature extraction unit, supplied with an electrocardiogram, said feature extraction unit configured for deriving features of cardiac events from said electrocardiogram and determining a feature vector, by a wavelet transform operating on said electrogram, describing waveform characteristics of cardiac events in said electrogram; and
   a clustering unit provided with said feature vector, said clustering unit configured for determining a distance between said feature vector and corresponding cluster feature vectors and assigning a cardiac event in said electrogram to a particular cluster that results in a minimum distance, as long as said minimum distance is less than a predetermined threshold value, and generating an output signal that identifies the particular cluster to which the cardiac event has been assigned.

2. An apparatus as claimed in claim 1 wherein each of said clusters is defined by a cluster center $\mu_i$ and a co-variance matrix $\Sigma_i$ for the cluster features of that cluster, and wherein said clustering unit determines a distance function D2 between each event feature vector and said cluster center $\mu_i$.

3. An apparatus as claimed in claim 2 wherein said clustering unit calculates said distance using Mahalanobis distance criterion.

4. An apparatus as claimed in claim 2 wherein said clustering unit determines said minimum distance by a grid search over a duration of the cardiac event.

5. An apparatus as claimed in claim 1 comprising an integrator that integrates said distance over a predetermined period of time.

6. An apparatus as claimed in claim 1 wherein said clustering unit updates said cluster feature according to a predetermined rule dependent on said minimum distance.

7. An apparatus as claimed in claim 1 wherein said clustering unit generates a new cluster if said minimum distance exceeds said predetermined threshold value, by setting features for said new cluster equal to the event features of the cardiac event that resulted in said minimum distance exceeding said predetermined threshold value.

8. An apparatus as claimed in claim 1 wherein said clustering unit terminates clusters that fail to have a predetermined number of cardiac events grouped therein within a predetermined time period.

9. An apparatus as claimed in claim 1 wherein said clustering unit performs a likelihood-based search sequence over said clusters to determine said minimum distance.

10. An apparatus as claimed in claim 1 wherein said clustering unit determines said minimum distance by a grid search only over clusters in which cardiac events have been grouped within a duration of the cardiac event.

11. An apparatus as claimed in claim 1 wherein said clustering unit calculates a distance of a cardiac event in question from a cluster in which a cardiac event was previously grouped.

12. An apparatus as claimed in claim 1 comprising a classifier that associates said clusters respectively with different cardiac rhythms according to predetermined rules.

13. A heart stimulator comprising:
- a pulse generator configured to interact with a subject to deliver stimulation pulses to the subject;
- an apparatus that analyzes cardiac events comprising a feature extraction unit, supplied with an electrocardiogram, said feature extraction unit configured for deriving features of cardiac events from said electrocardiogram and determining a feature vector, by a wavelet transform operating on said electrogram, describing waveform characteristics of cardiac events in said electrogram, and a clustering unit provided with said feature vector, said clustering unit configured for determining a distance between said feature vector and corresponding cluster feature vectors and assigning a cardiac event in said electrogram to a particular cluster that results in a minimum distance, as long as said minimum distance is less than a predetermined threshold value; and
- an arrhythmia detection and control unit connected to said pulse generator that controls emission of stimulation pulses from said pulse generator dependent on detection of an arrhythmia dependent on the cluster in which the cardiac event is grouped.

* * * * *